(12) United States Patent
de Oliveira et al.

(10) Patent No.: US 11,071,702 B2
(45) Date of Patent: Jul. 27, 2021

(54) HAIR CARE FORMULATION FROM CONCENTRATE

(71) Applicant: Dow Brasil Sudeste Industrial Ltda., Sao Paulo/Sp (BR)

(72) Inventors: Maria Rita de Oliveira, Sao Paulo (BR); Daisy de Fátima Scarparo de Sanctis, Sao Paulo (BR); Mayra Penna, Sao Paulo (BR)

(73) Assignee: Dow Brasil Sudeste Industrial LTDA, Sao Paulo/SP (BR)

(*) Notice: Subject to any disclaimer, the term of this patent is extended or adjusted under 35 U.S.C. 154(b) by 58 days.

(21) Appl. No.: 16/308,831

(22) PCT Filed: Jun. 29, 2017

(86) PCT No.: PCT/BR2017/050168
§ 371 (c)(1),
(2) Date: Dec. 11, 2018

(87) PCT Pub. No.: WO2018/000068
PCT Pub. Date: Jan. 4, 2018

(65) Prior Publication Data
US 2019/0192402 A1 Jun. 27, 2019

Related U.S. Application Data

(60) Provisional application No. 62/355,993, filed on Jun. 29, 2016.

(51) Int. Cl.
| | | |
|---|---|---|
| *A61K 8/39* | (2006.01) | |
| *A61K 8/37* | (2006.01) | |
| *A61K 8/73* | (2006.01) | |
| *A61K 8/81* | (2006.01) | |
| *A61K 8/86* | (2006.01) | |
| *A61Q 5/12* | (2006.01) | |

(52) U.S. Cl.
CPC .......... *A61K 8/39* (2013.01); *A61K 8/375* (2013.01); *A61K 8/731* (2013.01); *A61K 8/8182* (2013.01); *A61K 8/86* (2013.01); *A61Q 5/12* (2013.01); *A61K 2800/48* (2013.01); *A61K 2800/52* (2013.01); *A61K 2800/5426* (2013.01)

(58) Field of Classification Search
None
See application file for complete search history.

(56) References Cited

U.S. PATENT DOCUMENTS

| | | |
|---|---|---|
| 6,589,517 B1 | 7/2003 | McKelvey et al. |
| 2004/0115155 A1 | 6/2004 | Salvador et al. |
| 2011/0223124 A1 | 9/2011 | Drovetskaya et al. |
| 2015/0007853 A1* | 1/2015 | Krueger ............ A61Q 5/002 132/208 |

FOREIGN PATENT DOCUMENTS

| | | |
|---|---|---|
| EP | 2422763 A1 | 2/2012 |
| EP | 2532343 A1 | 12/2012 |
| WO | 9612467 A1 | 5/1996 |
| WO | 0191708 A1 | 12/2001 |
| WO | 02096381 A1 | 12/2002 |

* cited by examiner

*Primary Examiner* — Bethany P Barham
*Assistant Examiner* — Barbara S Frazier
(74) *Attorney, Agent, or Firm* — Thomas S. Deibert

(57) ABSTRACT

A method of making a hair care formulation is provided, comprising: providing a hair care system concentrate, comprising: 9 to 15 wt % of a cellulose based cationic polymer; 39 to 60 wt % a polyalkylene glycol; 9 to 15 wt % a film forming nonionic polyethylene glycol polymer; 2.5 to 20 wt % a linear polypropylene glycol; and 10 to 35 wt % a polyethylene glycol diester of stearic acid; providing at least one hair care additive; providing water; adding the hair care system concentrate and the at least one hair care additive to the water to form the hair care formulation.

9 Claims, No Drawings

HAIR CARE FORMULATION FROM CONCENTRATE

The present invention relates to a method of making a hair care formulation. In particular, the present invention relates to a method of making a hair care formulation using a hair care system concentrate, containing 9 to 15 wt % of a cellulose based cationic polymer; 39 to 60 wt % a polyalkylene glycol; 9 to 15 wt % a film forming nonionic polyethylene glycol polymer; 2.5 to 20 wt % a linear polypropylene glycol; and 10 to 35 wt % a polyethylene glycol diester of stearic acid; in combination with at least one hair care additive and water to form the hair care formulation.

When the cuticle of a hair is damaged, the hair becomes dry, loses shine and luster. Other signs of damaged hair include brittle or harsh texture, split ends, breakage, itchy scalp and loss of elasticity. Damaged hair tends to tangle easily and can be difficult to manage and style. Hair becomes damaged in a variety of ways. Hair is typically degraded to varying degrees by the action of atmospheric conditions or by treatments to the hair (e.g., bleaching, curling, straightening, coloring). Once damaged, hair becomes difficult to comb and style and may loose strength and elasticity.

To revitalize and repair the resultant damage to hair various hair care products are marketed for home and professional use. For example, a vast assortment of conditioning compositions have been formulated to impart the feel of softness or smoothness to the hair; to improve the luster, body, manageability, comb-ability of the hair; to impart the hair with increased elasticity and/or an overall appealing appearance. Conditioning of hair is effected by applying a composition to the hair that serves to impart hair with one of the noted properties.

Notwithstanding, there remains a need for improved hair conditioning formulations and methods of making the same, which methods expand the palate of easily incorporated ingredients to include the incorporation of ingredients with desirable hair care properties exhibiting physical-chemical properties that might otherwise limit their system compatibility and ease of incorporation. In particular, even where a given component might provide desirable performance, it may remain unavailable for formulators based on the difficult of incorporating that component into a final shelf stable composition. For instance, solid components lacking in water solubility face significant barriers for adoption in product formulations due to associated product processing complications.

The present invention provides a method of making a hair care formulation, comprising: providing a hair care system concentrate, comprising: 9 to 15 wt % of a cellulose based cationic polymer; 39 to 60 wt % a polyalkylene glycol; 9 to 15 wt % a film forming nonionic polyethylene glycol polymer; 2.5 to 20 wt % a linear polypropylene glycol; and, 10 to 35 wt % a polyethylene glycol diester of stearic acid; providing at least one hair care additive; providing water; adding the hair care system concentrate and the at least one hair care additive to the water to form the hair care formulation.

The present invention provides a method of making a hair care formulation, comprising: providing a hair care system concentrate, comprising: 9 to 15 wt % of a cellulose based cationic polymer; 39 to 60 wt % a polyalkylene glycol; 9 to 15 wt % a film forming nonionic polyethylene glycol polymer; 2.5 to 20 wt % a linear polypropylene glycol; and, 10 to 35 wt % a polyethylene glycol diester of stearic acid; providing at least one hair care additive; providing water; adding the at least one hair care additive to the water to an aqueous base formulation; and adding the hair care system concentrate to the aqueous base formulation to form the hair care formulation.

The present invention provides a method of making a hair care formulation, comprising: providing a hair care system concentrate, comprising: 9 to 15 wt % of a cellulose based cationic polymer, wherein the cellulose based cationic polymer in the hair care system concentrate provided is selected from the group consisting of polyquaterniums-10, polyquaterniums-24, polyquaterniums-27, polyquaterniums-67, polyquaterniums-72 and mixtures thereof, 39 to 60 wt % a polyalkylene glycol, wherein the polyalkylene glycol in the hair care system concentrate provided is according to formula I

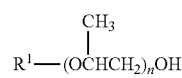

wherein $R^1$ is a $C_{2-20}$ alkyl group; and wherein n has an average value of 10 to 20; wherein n has an average value of 10 to 20; 9 to 15 wt % a film forming nonionic polyethylene glycol polymer, wherein the film forming nonionic polyethylene glycol polymer in the hair care system concentrate provided is according to formula II

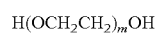

wherein m has an average value of 13,000 to 92,000; 2.5 to 20 wt % a linear polypropylene glycol, wherein the linear polypropylene glycol in the hair care system concentrate provided has an average of two terminal hydroxyl groups per molecule and a weight average molecular weight of 350 to 600 Daltons; and, 10 to 35 wt % a polyethylene glycol diester of stearic acid, wherein the polyethylene glycol diester of stearic acid in the hair care system concentrate provided is according to formula III

wherein x has an average value of 130 to 170; providing at least one hair care additive; providing water; adding the at least one hair care additive to the water to an aqueous base formulation; and adding the hair care system concentrate to the aqueous base formulation to form the hair care formulation.

DETAILED DESCRIPTION

We have found a unique method of making a hair care formulation that facilitates the ease incorporation of otherwise difficult to process components that impart the hair care formulation with a desirable hair conditioning property profile using a hair care system concentrate in combination with water and at least one hair care additive. The hair care formulations are suitable for use on different hair types and styles such as naturally dry hair, chemically damaged hair, curly hair, wavy Brazilian hair. etc. The hair care formulations preferably provide a balance of conditioning, moisturizing and lubricity features imparting multi-functionality and easy of use for conditioning, repairing and revitalizing hair.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and polyacrylic acid standards. GPC techniques are discussed in detail in Modem Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons.

The term "polymer" as used herein and in the appended claims refers to a compound prepared by polymerizing monomers, whether of the same or a different type. The generic term "polymer" includes the terms "homopolymer," "copolymer," and "terpolymer."

The term "hair care" as used herein and in the appended claims relates to concentrates formulated for use in the preparation of compositions for topical application to hair, in particular, to human hair. Examples of such compositions include, but are not limited to, hair conditioners (e.g., leave on hair conditioners, rinse off hair conditioners); shampoos; styling gels; hair masks; ampoules; detangling sprays; serums; lotions and combing creams.

The term "cosmetically acceptable" as used herein and in the appended claims refers to ingredients typically used in hair care compositions, and is intended to underscore that materials that are toxic when present in the amounts typically found in hair care compositions are not contemplated as part of the present invention.

The term "stable" as used herein and in the appended claims in reference to the hair care system concentrate means that the hair care system concentrate does not display syneresis apparent by unaided visual observation.

The term "storage stable" as used herein and in the appended claims in reference to the hair care system concentrate means that the hair care system concentrate does not display syneresis apparent by unaided visual observation during storage of the hair care system concentrate at 25° C. for a period of at least twelve (12) weeks.

The term "enhanced storage stability" as used herein and in the appended claims in reference to the hair care system concentrate means that the hair care system concentrate does not display syneresis apparent by unaided visual observation during storage of the hair care system concentrate at a temperature of 5 to 45° C. for a period of at least twelve (12) weeks.

Preferably, the method of making a hair care formulation of the present invention, comprises: providing a hair care system concentrate, comprising: 9 to 15 wt % (preferably, 10 to 14; more preferably 11 to 13; most preferably, 12 wt %) of a cellulose based cationic polymer(preferably, wherein the cellulose based cationic polymer is selected from the group consisting of polyquatemium-10, polyquaterniums-24, polyquatemium-27, polyquaternium-67, polyquaternium-72 and mixtures thereof); 39 to 60 wt % (preferably, 45 to 58 wt %; more preferably, 51 to 53 wt %; most preferably, 52 wt %) a polyalkylene glycol (preferably, wherein the polyalkylene glycol is according to formula I

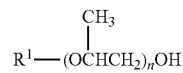

wherein $R^1$ is a $C_{2-20}$ alkyl group (preferably, a $C_{4-18}$ alkyl group; more preferably, a $C_{4-10}$ alkyl group; most preferably, a $C_4$ alkyl group); and wherein n has an average value of 10 to 20 (preferably, 12 to 16; more preferably, 13 to 15; most preferably, 14)); 9 to 15 wt % (preferably, 10 to 14; more preferably 11 to 13; most preferably, 12 wt %) a film forming nonionic polyethylene glycol polymer (preferably, wherein the film forming nonionic polyethylene glycol polymer is according to formula II

wherein m has an average value of 13,000 to 92,000 (preferably, 35,000 to 80,000; more preferably, 40,000 to 50,000; yet more preferably, 42,000 to 47,000; most preferably, 44,000 to 46,000)); 2.5 to 20 wt % (preferably, 2.5 to 10 wt %; more preferably, 3 to 7.5 wt %; yet more preferably, 4 to 6 wt %; most preferably, 5 wt %) a linear polypropylene glycol(preferably, wherein the linear polypropylene glycol has an average of two terminal hydroxyl groups per molecule and a weight average molecular weight of 350 to 600 Daltons)); and, 10 to 35 wt % (preferably, 16 to 25 wt %; more preferably, 18 to 20 wt %; most preferably, 19 wt %) a polyethylene glycol diester of stearic acid (preferably, wherein the polyethylene glycol diester of stearic acid is according to formula III

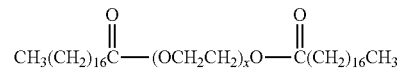

wherein x has an average value of 130 to 170 (preferably, 140 to 160; more preferably, 145 to 155; most preferably, 150)); providing at least one hair care additive; providing water; adding the hair care system concentrate and the at least one hair care additive to the water to form the hair care formulation (preferably, wherein the at least one hair care additive is added to the water to form an aqueous base formulation; and then the hair care system concentrate is added to the aqueous base formulation to form the hair care formulation).

Preferably, in the method of making a hair care formulation of the present invention, the hair care system concentrate provided, comprises: 9 to 15 wt % (preferably, 10 to 14; more preferably 11 to 13; most preferably, 12 wt %) of a cellulose based cationic polymer (preferably, wherein the cellulose based cationic polymer is selected from the group consisting of polyquatemium-10, polyquaterniums-24, polyquaternium-27, polyquaternium-67, polyquaternium-72 and mixtures thereof); 39 to 60 wt % (preferably, 45 to 58 wt %; more preferably, 51 to 53 wt %; most preferably, 52 wt %) a polyalkylene glycol (preferably, wherein the polyalkylene glycol is according to formula I

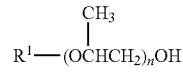

wherein $R^1$ is a $C_{2-20}$ alkyl group (preferably, a $C_{4-18}$ alkyl group; more preferably, a $C_{4-10}$ alkyl group; most preferably, a $C_4$ alkyl group); and wherein n has an average value of 10 to 20 (preferably, 12 to 16; more preferably, 13 to 15; most preferably, 14); 9 to 15 wt % (preferably, 10 to 14; more preferably 11 to 13; most preferably, 12 wt %) a film forming nonionic polyethylene glycol polymer (preferably, wherein the film forming nonionic polyethylene glycol polymer is according to formula II $$H(OCH_2CH_2)_mOH \qquad\qquad II$$

wherein m has an average value of 13,000 to 92,000 (preferably, 35,000 to 80,000; more preferably, 40,000 to 50,000; yet more preferably, 42,000 to 47,000; most preferably, 44,000 to 46,000); 2.5 to 20 wt % (preferably, 2.5 to 10 wt %; more preferably, 3 to 7.5 wt %; yet more preferably, 4 to 6 wt %; most preferably, 5 wt %) a linear polypropylene glycol (preferably, wherein the linear polypropylene glycol has an average of two terminal hydroxyl groups per molecule and a weight average molecular weight of 350 to 600 Daltons); and, 10 to 35 wt % (preferably, 16 to 25 wt %; more preferably, 18 to 20 wt %; most preferably, 19 wt %) a polyethylene glycol diester of stearic acid (preferably, wherein the polyethylene glycol diester of stearic acid is according to formula III $$CH_3(CH_2)_{16}\overset{O}{\overset{\|}{C}}-(OCH_2CH_2)_xO-\overset{O}{\overset{\|}{C}}(CH_2)_{16}CH_3 \qquad III$$

wherein x has an average value of 130 to 170 (preferably, 140 to 160; more preferably, 145 to 155; most preferably, 150)).

Preferably, in the method of making a hair care formulation of the present invention, the hair care system concentrate provided is stable. More preferably, in the method of making a hair care formulation of the present invention, the hair care system concentrate provided is storage stable. Most preferably, in the method of making a hair care formulation of the present invention, the hair care system concentrate provided has enhanced storage stability.

Preferably, in the method of making a hair care formulation of the present invention, the cellulose based cationic polymer used in the hair care system concentrate provided is a cosmetically acceptable cellulose based cationic polymer. More preferably, in the method of making a hair care formulation of the present invention, the cellulose based cationic polymer used in the hair care system concentrate provided is a cosmetically acceptable cellulose based cationic polymer, wherein the cellulosed based cationic polymer is selected from the group consisting of polyquatemium-10, polyquaterniums-24, polyquaternium-27, polyquaternium-67, polyquaternium-72 and mixtures thereof. Most preferably, the cellulose based cationic polymer is polyquatemium-67.

Preferably, in the method of making a hair care formulation of the present invention, the hair care system concentrate provided contains 9 to 15 wt % of a cellulose based cationic polymer. More preferably, in the method of making a hair care formulation of the present invention, the hair care system concentrate provided contains 10 to 14 wt % of a cellulose based cationic polymer. Still more preferably, in the method of making a hair care formulation of the present invention, the hair care system concentrate provided contains 11 to 13 wt % of a cellulose based cationic polymer.

Most preferably, in the method of making a hair care formulation of the present invention, the hair care system concentrate provided contains 12 wt % of a cellulose based cationic polymer.

Preferably, in the method of making a hair care formulation of the present invention, the polyalkylene glycol used in the hair care system concentrate provided is a cosmetically acceptable polyalkylene glycol. More preferably, in the method of making a hair care formulation of the present invention, the polyalkylene glycol used in the hair care system concentrate provided is a cosmetically acceptable polyalkylene glycol, wherein the polyalkylene glycol is according to formula I $$R^1-(\overset{\overset{\displaystyle CH_3}{|}}{O}CHCH_2)_nOH \qquad\qquad I$$

wherein $R^1$ is a $C_{2-20}$ alkyl group (preferably, a $C_{4-18}$ alkyl group; more preferably, a $C_{4-10}$ alkyl group; most preferably, a $C_4$ alkyl group); and wherein n has an average value of 10 to 20 (preferably, 12 to 16; more preferably, 13 to 15; most preferably, 14). Most preferably, the polyalkylene glycol is according to the formula I, wherein n has an average value of 12 to 16.

Preferably, in the method of making a hair care formulation of the present invention, the hair care system concentrate provided contains 39 to 60 wt % of a polyalkylene glycol. More preferably, in the method of making a hair care formulation of the present invention, the hair care system concentrate provided contains 45 to 58 wt % of a polyalkylene glycol. Still more preferably, in the method of making a hair care formulation of the present invention, the hair care system concentrate provided contains 51 to 53 wt % of a polyalkylene glycol. Most preferably, the hair care system concentrate provided contains 52 wt % of a polyalkylene glycol.

Preferably, in the method of making a hair care formulation of the present invention, the film forming nonionic polyethylene glycol polymer used in the hair care system concentrate provided is a cosmetically acceptable film forming nonionic polyethylene glycol polymer. Preferably, in the method of making a hair care formulation of the present invention, the film forming nonionic polyethylene glycol polymer used in the hair care system concentrate provided is a cosmetically acceptable film forming nonionic polyethylene glycol polymer, wherein the film forming nonionic polyethylene glycol polymer is according to formula II $$H(OCH_2CH_2)_mOH \qquad\qquad II$$

wherein m has an average value of 13,000 to 92,000. More preferably, in the method of making a hair care formulation of the present invention, the film forming nonionic polyethylene glycol polymer used in the hair care system concentrate provided is a cosmetically acceptable film forming nonionic polyethylene glycol polymer, wherein the film forming nonionic polyethylene glycol polymer is according to formula II, wherein m has an average value of 35,000 to 80,000. Still more preferably, the film forming nonionic polyethylene glycol polymer used in the hair care system concentrate provided is a cosmetically acceptable film forming nonionic polyethylene glycol polymer, wherein the film forming nonionic polyethylene glycol polymer is according to formula II, wherein m has an average value of 40,000 to 50,000. Yet still more preferably, the film forming nonionic polyethylene glycol polymer used in the hair care system concentrate provided is a cosmetically acceptable film forming nonionic polyethylene glycol polymer, wherein the film forming nonionic polyethylene glycol polymer is according to formula II, wherein m has an average value of 42,000 to 47,000. Most preferably, the film fainting nonionic polyethylene glycol polymer used in the hair care system concentrate provided is a cosmetically acceptable film forming nonionic polyethylene glycol polymer, wherein the film forming nonionic polyethylene glycol polymer is according to formula II, wherein m has an average value of 44,000 to 46,000.

Preferably, in the method of making a hair care formulation of the present invention, the hair care system concentrate provided contains 9 to 15 wt % of a film forming nonionic polyethylene glycol polymer. More preferably, the hair care system concentrate provided contains 10 to 14 wt % of a film forming nonionic polyethylene glycol polymer. Still more preferably, the hair care system concentrate provided contains 11 to 13 wt % of a film forming nonionic polyethylene glycol polymer. Most preferably, the hair care system concentrate provided contains 12 wt % of a film forming nonionic polyethylene glycol polymer.

Preferably, in the method of making a hair care formulation of the present invention, the linear polypropylene glycol used in the hair care system concentrate provided is a cosmetically acceptable linear polypropylene glycol. More preferably, the linear polypropylene glycol used in the hair care system concentrate provided is a cosmetically acceptable linear polypropylene glycol, wherein the linear polypropylene glycol has an average of two terminal hydroxyl groups per molecule and a weight average molecular weight of 350 to 600 Daltons. Still more preferably, the linear polypropylene glycol used in the hair care system concentrate provided is a cosmetically acceptable linear polypropylene glycol, wherein the linear polypropylene glycol has an average of two terminal hydroxyl groups per molecule and a weight average molecular weight of 410 to 440 Daltons. Yet still more preferably, the linear polypropylene glycol used in the hair care system concentrate provided is a cosmetically acceptable linear polypropylene glycol, wherein the linear polypropylene glycol has an average of two terminal hydroxyl groups per molecule and a weight average molecular weight of 420 to 430 Daltons. Most preferably, the linear polypropylene glycol used in the hair care system concentrate provided is a cosmetically acceptable linear polypropylene glycol, wherein the linear polypropylene glycol has an average of two terminal hydroxyl groups per molecule and a weight average molecular weight of 425 Daltons.

Preferably, in the method of making a hair care formulation of the present invention, the hair care system concentrate provided contains 2.5 to 20 wt % of a linear polypropylene glycol. More preferably, in the method of making a hair care formulation of the present invention, the hair care system concentrate provided contains 2.5 to 10 wt % of a linear polypropylene glycol. Yet more preferably, the hair care system concentrate of the present invention contains 3 to 7 wt % of a linear polypropylene glycol. Still more preferably, the hair care system concentrate provided contains 4 to 6 wt % of a linear polypropylene glycol. Most preferably, the hair care system concentrate provided contains 5 wt % of a linear polypropylene glycol.

Preferably, in the method of making a hair care formulation of the present invention, the polyethylene glycol diester of stearic acid used in the hair care system concentrate provided is a cosmetically acceptable polyethylene glycol diester of stearic acid. More preferably, the polyethylene glycol diester of stearic acid used in the hair care system concentrate provided is a cosmetically acceptable polyethylene glycol diester of stearic acid, wherein the polyethylene glycol diester of stearic acid is according to formula III

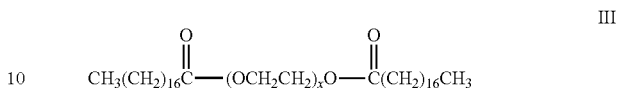

wherein x has an average value of 130 to 170. Still more preferably, the polyethylene glycol diester of stearic acid used in the hair care system concentrate provided is a cosmetically acceptable polyethylene glycol diester of stearic acid, wherein the polyethylene glycol diester of stearic acid is according to formula III, wherein x has an average value of 140 to 160. Yet still more preferably, the polyethylene glycol diester of stearic acid used in the hair care system concentrate provided is a cosmetically acceptable polyethylene glycol diester of stearic acid, wherein the polyethylene glycol diester of stearic acid is according to formula III, wherein x has an average value of 145 to 155. Most preferably, the polyethylene glycol diester of stearic acid used in the hair care system concentrate provided is a cosmetically acceptable polyethylene glycol diester of stearic acid, wherein the polyethylene glycol diester of stearic acid is according to formula III, wherein x has an average value of 150.

Preferably, in the method of making a hair care formulation of the present invention, the hair care system concentrate provided contains 10 to 35 wt % of a polyethylene glycol diester of stearic acid. More preferably, the hair care system concentrate provided contains 16 to 25 wt % of a polyethylene glycol diester of stearic acid. Still more preferably, the hair care system concentrate provided contains 18 to 20 wt % of a polyethylene glycol diester of stearic acid. Most preferably, the hair care system concentrate provided contains 19 wt % of a polyethylene glycol diester of stearic acid.

Preferably, in the method of making a hair care formulation of the present invention, the hair care system concentrate is provided by providing a cellulose based cationic polymer (preferably, wherein the cellulose based cationic polymer is a cosmetically acceptable cellulosed based cationic polymer selected from the group consisting of polyquaternium-10, polyquaternium-24, polyquaternium-27, polyquaternium-67, polyquaternium-72 and mixtures thereof); providing a polyalkylene glycol (preferably, wherein the polyalkylene glycol is a cosmetically acceptable polyalkylene glycol according to formula I

wherein $R^1$ is a $C_{2-20}$ alkyl group (preferably, a $C_{4-18}$ alkyl group; more preferably, a $C_{4-10}$ alkyl group; most preferably, a $C_4$ alkyl group); and wherein n has an average value of 10 to 20 (preferably, 12 to 16; more preferably, 13 to 15; most preferably, 14)); providing a film forming nonionic polyethylene glycol polymer (preferably, wherein the film forming nonionic polyethylene glycol polymer is a cosmetically acceptable polyalkylene glycol according to formula II

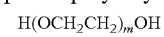

wherein in has an average value of 13,000 to 92,000 (preferably, 35,000 to 80,000; more preferably, 40,000 to 50,000; yet more preferably, 42,000 to 47,000; most preferably, 44,000 to 46,000)); providing a linear polypropylene glycol (preferably, wherein the linear polypropylene glycol is a cosmetically acceptable linear polypropylene glycol having an average of two terminal hydroxyl groups per molecule and a weight average molecular weight of 350 to 600 Daltons); providing a polyethylene glycol diester of stearic acid (preferably, wherein the polyethylene glycol diester of stearic acid is a cosmetically acceptable polyethylene glycol diester of stearic acid according to formula III

wherein x has an average value of 130 to 170 (preferably, 140 to 160; more preferably, 145 to 155; most preferably, 150)); heating the linear polypropylene glycol and the polyethylene glycol diester of stearic acid to ≥65° C. (preferably, 65 to 100° C.; more preferably, 65 to 80° C.; most preferably, 70 to 75° C.); combining the linear polypropylene glycol and the polyethylene glycol diester of stearic acid (preferably, with agitation) to form a combination; then adding the polyalkylene glycol to the combination (preferably, with continued agitation) while allowing the temperature of the combination to cool to ≤45° C.; and, then adding the cellulose based cationic polymer and the film forming nonionic polyethylene glycol polymer to the combination (preferably, with continued agitation) to form the hair care system concentrate provided.

Preferably, in the method of making a hair care formulation of the present invention, the hair care formulation formed contains 0.1 to 5 wt % of the hair care system concentrate. More preferably, in the method of making a hair care formulation of the present invention, the hair care formulation formed contains 0.5 to 3 wt % of the hair care system concentrate. Still more preferably, in the method of making a hair care formulation of the present invention, the hair care formulation formed contains 0.75 to 2.5 wt % of the hair care system concentrate. Yet still more preferably, in the method of making a hair care formulation of the present invention, the hair care formulation formed contains 1 to 2.25 wt % of the hair care system concentrate. Most preferably, in the method of making a hair care formulation of the present invention, the hair care formulation formed contains 1.5 to 2.0 wt % of the hair care system concentrate.

Preferably, in the method of making a hair care formulation of the present invention, the at least one hair care additive provided comprises at least one of a surfactant/emulsifier (e.g., a nonionic surfactant (e.g., trideceth-6, trideceth-12, polysorbate-20, polysorbate-40, polysorbate-60, polysorbate-80 and ceteareth-20), a cationic surfactant (e.g., cetrimonium chloride, behentrimonium chloride, benhentrimonium methosulfate, Quaternium-18)); a conditioning agent/emollient (e.g., stearamidopropyldimethyl amine, stearyl alcohol, behentrimonium chloride, benhentrimonium methosulfate, cetyl alcohol, propylene glycol, methyl gluceth-10, hydrocarbon oil, ester, natural oil/plant extract/protein/amino acid (e.g., argania spinosa kernel oil, glycine soja, hydrolyzed wheat starch, hydrolyzed wheat protein, cysteine, wheat amino acids, theobroma cacao bean extract, meadowfoam seed oil, olive fruit oil, prunus amygdalus dulcis), silicone (e.g., amodimethicone, his aminopropyl dimethicone, cyclopentasiloxane, cyclohexasiloxane, dimethicone)); a wax (e.g., fatty alcohol, fatty acid, glyceryl stearate); a sensory modifier; a lubricant; an antimicrobial agent/preservative (e.g., benzoic acid, sorbic acid, phenoxyethanol, benzyl alcohol, methylchloroisothiazolinone, methylisothiazolinone); an antioxidant (e.g., butylated hydroxytoluene); a chelating agent; a humectant (e.g., glycerin, sorbitol, monoglycerides, lecithins, glycolipids, polysaccharides, plant extract/protein/amino acid/a vitamin (e.g., glycine soja, hydrolyzed wheat starch, hydrolyzed wheat protein, cysteine, wheat amino acids, theobroma cacao bean extract, vitamin E), diols (e.g., propylene glycol), diol analogs, triols, triol analogs, polymeric polyols); an opacifying agent; a formulation aid (e.g., an emulsifier, a thickening agent (e.g., polysaccharides (e.g., xanthan gum, guar gum, starch, and vegetable gum), cellulosic polymers (e.g., carboxymethyl cellulose (CMC), hydroxymethyl cellulose (HMC), hydroxypropyl methyl cellulose (HPMC)), hydrophobically modified cross-linked acrylate copolymers (e.g., those sold by Lubrizol under the trademark Carbopol® Ultrez 21)), a foam stabilizer, a viscosity builder, a sequestrate, a suspending agent, pH adjusting agent, a buffer, a neutralizing agent); a hair care active (e.g., an antidandruff agent; a sunscreen (e.g., UV filter/absorber such as bensophenone-4, ethyhexyl methoxycinnamate), a penetrant, a hair fixative, an antifrizz agent, an antistatic agent (e.g., panthenyl ethyl ether), a hair waving/straightening agent, a colorant); a lubricant (e.g., panthenol); a chelating agent/sequestrate (e.g., disodium EDTA, trisodium ethylenediamine disuccinate); a fragrance (e.g., limonene, linalool, citranellol); a vitamin (Vitamine E); a film former; a vehicle (e.g., a propellant) and a solid (e.g., mica, titanium dioxide, iron oxide). One of ordinary skill in the art will recognize that some additives can fall within more than one general category of hair care additive. More preferably, in the method of making a hair care formulation of the present invention, the at least one hair care additive provided comprises at least one of a surfactant, a conditioning agent/emollient, an antimicrobial agent/preservative, an antioxidant, a humectant, an opacifying agent, an emulsifier, a thickening agent, a foam stabilizer, a viscosity builder, a sequestrate, a suspending agent, a pH control agent, an antidandruff agent, a sunscreen and a fragrance.

Preferably, in the method of making a hair care formulation of the present invention, wherein the hair care formulation is a rinse off hair conditioner; the at least one hair care additive provided comprises at least one of stearyl alcohol, behentrimonium chloride, cetyl alcohol, bis aminopropyl dimethicone, a fragrance, benzyl alcohol, methylchloroisothiazolinone, methylisothiazolinone, panthenol, panthenyl ethyl ether, disodium ethylenediaminetetraacetic acid, trisodium ethylenediamine disuccinate and argania spinosa kernel oil.

Preferably, in the method of making a hair care formulation of the present invention, wherein the hair care formulation is a leave on hair conditioner; the at least one hair care additive provided comprises at least one of amodimethicone, glycine soja, hydrolyzed wheat protein, cysteine, wheat amino acids, trideceth-12, cetrimonium chloride, polysorbate-20, quaternium-18, propylene glycol, methyl gluceth-10, hydrolyzed wheat starch, panthenol, theobroma cacao bean extract, limonene, linalool, citranellol, bensophenone-4, disodium ethylenediaminetetraacetic acid, methylparaben, methylchloroisothiazolinone and methylisothiasolinone.

Preferably, in the method of making a hair care formulation of the present invention, wherein the hair care formulation is a hair mask; the at least one hair care additive provided comprises at least one of cetearyl alcohol, behentrimonium chloride, cyclopentasiloxane, dimethicone, ethylhexyl isononanoate, behenyl alcohol, meadow foam seed oil (limnanthes alba), cyclohexasiloxane, olive fruit oil (plea europaea), prunus amygdalus dulcis (sweet almond oil), stearamidopropyl dimethylamine, behentrimonium methosulfate, amodimethicone, panthenol, glycol stearate, ceteth-2, hydroxyethylcellulose, phenoxyethanol, methylparaben, propylparaben, citric acid, mica, titanium dioxide, iron oxide and fragrance.

Preferably, in the method of making a hair care formulation of the present invention, wherein the hair care formulation is a combing cream; the at least one hair care additive provided comprises at least one of cyclomethicone, jojoba ester, dimethicone copolyol (silica), nonfat dry milk, soy protein, stearic acid, capric/caprylic stearic triglyceride, jojoba oil, hybrid sunflower oil, cetearyl alcohol, glyceryl stearate, PEG-40 stearate, aloe vera (aloe babadensis) gel, acrylates/$C_{10-30}$ alkyl acrylate crosspolymer, propylene glycol, tocopheryl acetate (Vitamin E), methylparaben, propylparaben and fragrance.

Some embodiments of the present invention will now be described in detail in the following Examples.

Examples 1-2

Preparation Hair Care System Concentrate

In each of Examples 1-2, a hair care system concentrate having the composition noted in TABLE 1 was prepared in a flask outfitted with a heating mantle and a stirring bar. PPG-9 (Polyglycol P425 "P" series polyglycol available from The Dow Chemical Company) was added to the flask and heated to a temperature of 70 to 75° C. Then PEG 150 distearate (Aculyn™ 60 polymer available from The Dow Chemical Company) was added to the flask with stirring for about 10 minutes while maintaining the temperature set point at 70 to 75° C. to provide a homogenous mixture. The heating mantle was then removed from the flask and PPG-14 butyl ether (Ucon™ fluid AP available from The Dow Chemical Company) was introduced to the flask contents slowly over a period of about 10 minutes with continued stirring. The flask contents were then allowed to continue cooling to 45° C. A premixture of polyquaternium-67 (Softcat™ SX Polymer SX-1300X available from The Dow Chemical Company) and PEG-45M (Polyox™ WSR N60K available from The Dow Chemical Company) were then slowly added to the flask contents with continued stirring. Then continue stirring the contents of the flask for 40 to 50 minutes to provide the product hair care system concentrate.

TABLE 1

| Component | | Final system concentration (wt %) | |
|---|---|---|---|
| INCI Name | Commercial Name[a] | Ex. 1 | Ex. 2 |
| PPG-9 | Polyglycol P425 | 5.0 | 18.0 |
| PPG-14 butyl ether | Ucon™ Fluid AP | 52.0 | 42.0 |
| Polyquaternium-67 | Softcat™ SX Polymer SX-1300X | 12.0 | 15.0 |
| PEG-45M | Polyox™ WSR N60K | 12.0 | 15.0 |
| PEG150 Distearate | Aculyn™ 60 polymer | 19.0 | 10.0 |

[a]Available from The Dow Chemical Company

Stability Evaluations

The stability of a hair care system concentrates prepared according to Examples 1 and 2 were evaluated over a three month period. Each of the hair care system concentrates was divided into three samples. One sample was maintained at 5° C. over the three month period. A second sample was maintained at 25° C. over the three month period. A third sample was maintained at 45° C. over the three month period. The evaluation included a visual assessment and an evaluation of the rheological behavior of each of the three samples of the hair care system concentrate. Visual inspection of the samples over the three month period showed no syneresis in any of the samples. The visual inspection did show some yellowing of the hair care system concentrate over the three month period in the sample maintained at 45° C. The rheological behavior of the sample of the hair care system concentrate maintained at 25° C. remained unchanged over the thirty day period. A slight drop in the viscosity was observed for the samples of the hair care system concentrate maintained at 5° C. and at 45° C.

Comparative Example C1

Order of Addition

Comparative combinations having the same composition noted in TABLE 1 were prepared using the same flask outfitted with a heating mantle and a stirring bar as used in Example 1. In the comparative combinations of Comparative Example C1, the order of addition of the various components were modified. From these comparative combinations, it was determined critical that the PEG150 Distearate be added to the flask before the PPG-14 butyl ether, the polyquaterniums-67 and the PEG-45M to avoid liquid separation or syneresis in the product obtained.

Comparative Example C2

Temperature when Added

Comparative combinations having the same composition noted in TABLE 1 were prepared using the same flask outfitted with a heating mantle and a stirring bar as used in Example 1. In the comparative combinations of Comparative Example C2, the components were added to the flask in the same order as in Example 1. In contrast to Example 1, however, the temperature of the flask contents were >45° C. when the polyquaterniums-67 and the PEG-45M were added to the flask in each of the comparative combinations of Comparative Example C2, resulting in a thick paste.

Comparative Example C3

Film Forming Nonionic Polyethylene Glycol Polymer

Comparative combinations having the same composition noted in TABLE 1 with the exception that the PEG-45M was substituted with PEG-90M (Polyox™ WSR N301 available from The Dow Chemical Company) was prepared using the same flask outfitted with a heating mantle and a stirring bar as used in Example 1. The resulting composition was extremely elastic and was amenable to pumping.

Comparative Example C4

Polyethylene Glycol Diester of Stearic Acid Concentration

A plurality of hair care system concentrates were prepared having the same component content as present in Example 1 with the exception that the amount of PEG150 distearate added was varied to provide a dosage concentration thereof in the final system concentrate ranging from 3 to 20 wt %. The hair care system concentrates having a PEG150 distearate concentration of 10 to 19 wt % were observed not to exhibit syneresis.

Example 3

Hair Care Formulation

A hair care formulation having the composition noted in TABLE 2 was prepared by combining a hair care system concentrate prepared according to Example 1 with an aqueous base formulation, wherein the aqueous base formulation contained the hair care additives noted in TABLE 2 dispersed in water.

TABLE 2

| Ingredient | wt % |
| --- | --- |
| Stearamidopropyl dimethylamine (surfactant/emollient/conditioning agent) | 1.50 |
| Cethearyl alcohol (wax/conditioning agent) | 5.00 |
| Lactic acid, 85% (formulation aid) | 0.52 |
| BHT (antioxidant) | 0.05 |
| Dissodium EDTA (chelating agent) | 0.10 |
| Behentrimonium chloride (surfactant/conditioning agent) | 0.30 |
| Preservative | 0.50 |
| Hair care system concentrate | 1.50 |

We claim:

1. A method of making a hair care formulation, comprising:
providing a hair care system concentrate by
providing 9 to 15 wt %, based on weight of the hair care system concentrate, of a cellulose based cationic polymer, wherein the cellulose based cationic polymer is selected from the group consisting of polyquaternium-10, polyquaterniums-24, polyquaternium-27, polyquaternium-67, polyquaternium-72 and mixtures thereof;
providing 39 to 60 wt %, based on weight of the hair care system concentrate, of a polyalkylene glycol, wherein the polyalkylene glycol in the hair care system concentrate provided is according to formula I

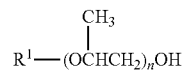

wherein $R^1$ is a $C_{2-20}$ alkyl group; and wherein n has an average value of 10 to 20;
providing 9 to 15 wt %, based on weight of the hair care system concentrate, of a film forming nonionic polyethylene glycol polymer, wherein the film forming nonionic polyethylene glycol polymer in the hair care system concentrate provided is according to formula II

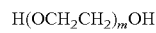

wherein m has an average value of 13,000 to 92,000;
providing 2.5 to 20 wt %, based on weight of the hair care system concentrate, of a linear polypropylene glycol, wherein the linear polypropylene glycol has an average of two terminal hydroxyl groups per molecule and a weight average molecular weight of 350 to 600 Daltons;
providing 10 to 35 wt %, based on weight of the hair care system concentrate, of a polyethylene glycol diester of stearic acid, wherein the polyethylene glycol diester of stearic acid in the hair care system concentrate provided is according to formula III

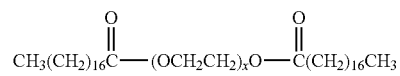

wherein x has an average value of 130 to 170;
heating the linear polypropylene glycol and the polyethylene glycol diester of stearic acid to 65 to 80° C.;
combining the linear polypropylene glycol and the polyethylene glycol diester of stearic acid to form a combination;
then adding the polyalkylene glycol to the combination while allowing the temperature of the combination to cool to less than or equal to 45° C.; and
then adding the cellulose based cationic polymer and the film forming nonionic polyethylene glycol polymer to the combination to form the hair care system concentrate;
providing at least one hair care additive; wherein the at least one hair care additive comprises at least one of a surfactant, a conditioning agent, an emollient, a humectant, an emulsifier, an opacifying agent, a thickening agent, a foam stabilizer, a viscosity builder, a preservative, a sequestrate, an antioxidant, an antidandruff agent, a suspending agent, a pH control agent, a protein, a fragrance, a sunscreen and a botanical extract;
providing water;
adding the hair care system concentrate and the at least one hair care additive to the water to form the hair care formulation.

2. The method of claim 1,
wherein the cellulose based cationic polymer in the hair care system concentrate provided is polyquaterniums-67;
wherein n has an average value of 12 to 16;
wherein m has an average value of 44,000 to 46,000;

wherein the linear polypropylene glycol in the hair care system concentrate provided has a weight average molecular weight of 420 to 430 Daltons; and, wherein x has an average value of 140 to 160.

3. The method of claim 1,
wherein the cellulose based cationic polymer in the hair care system concentrate provided is polyquaternium-67;
wherein $R^1$ is a $C_4$ alkyl group; and wherein n has an average value of 12 to 16;
wherein m has an average value of 42,000 to 47,000;
wherein the linear polypropylene glycol in the hair care system concentrate provided has a weight average molecular weight of 400 to 450 Daltons;
wherein x has an average value of 140 to 160.

4. The method of claim 1, wherein the hair care system concentrate provided accounts for 0.1 to 2 wt % of the hair care formulation and wherein the at least one hair care additive is added to the water to form an aqueous base formulation; and
wherein the hair care system concentrate is then added to the aqueous base formulation to form the hair care formulation.

5. The method of claim 4, wherein the hair care formulation is selected from the group consisting of a leave on hair conditioner and a rinse off hair conditioner.

6. The method of claim 4,
wherein the hair care formulation is a rinse off hair conditioner, and
wherein the at least one hair care additive provided comprises at least one of a stearyl alcohol, behentrimonium chloride, cetyl alcohol, bis aminopropyl dimethicone, a fragrance, benzyl alcohol, methylchloroisothiazolinone, methylisothiazolinone, panthenol, panthenyl ethyl ether, disodium EDTA, trisodium ethylenediamine disuccinate and argania spinosa kernel oil.

7. The method of claim 4,
wherein the hair care formulation is a leave on hair conditioner, and
wherein the at least one hair care additive provided comprises at least one of amodimethicone, glycine soja, hydrolyzed wheat protein, cysteine, wheat amino acids, trideceth-12, cetrimonium chloride, polysorbate-20, quaternium-18, propylene glycol, methyl gluceth-10, hydrolyzed wheat starch, panthenol, theobroma cacao bean extract, limonene, linalool, citronellol, bensophenone-4, disodium EDTA, methylparaben, methylchloroisothiazolinone and methylisothiasolinone.

8. The method of claim 4,
wherein the hair care formulation is a hair mask, and
wherein the at least one hair care additive provided comprises at least one of cetearyl alcohol, behentrimonium chloride, cyclopentasiloxane, dimethicone, ethylhexyl isononanoate, behenyl alcohol, meadowfoam seed oil, cyclohexasiloxane, olive fruit oil, prunus amygdalus dulcis, stearamidopropyl dimethylamine, behentrimonium methosulfate, amodimethicone, panthenol, glycol stearate, ceteth-2, hydroxyethylcellulose, phenoxyethanol, methylparaben, propylparaben, citric acid, mica, titanium dioxide, iron oxide, and fragrance.

9. The method of claim 4,
wherein the hair care formulation is a combing cream, and
wherein the at least one hair care additive provided comprises at least one of cyclomethicone, jojoba ester, dimethicone copolyol, nonfat dry milk, soy protein, stearic acid, capric/caprylic stearic triglyceride, jojoba oil, hybrid sunflower oil, cetearyl alcohol, glyceryl stearate, PEG-40 stearate, aloe vera gel, acrylates/$C_{10-30}$ alkyl acrylate crosspolymer, propylene glycol, tocopheryl acetate, methylparaben, propylparaben, and fragrance.

* * * * *